(12) United States Patent
Stasch et al.

(10) Patent No.: US 6,903,089 B1
(45) Date of Patent: Jun. 7, 2005

(54) LACTAM-SUBSTITUTED PYRAZOLOPYRIDINE DERIVATIVES

(75) Inventors: Johannes-Peter Stasch, Solingen (DE); Achim Feurer, Wilhelmsfeld (DE); Stefan Weigand, Wuppertal (DE); Elke Stahl, Bergisch Gladbach (DE); Dietmar Flubacher, Freiburg (DE); Cristina Alonso-Alija, Haan (DE); Frank Wunder, Wuppertal (DE); Dieter Lang, Velbert (DE); Klaus Dembowsky, Boston, MA (US); Alexander Straub, Wuppertal (DE); Elisabeth Perzborn, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/432,740

(22) PCT Filed: Nov. 9, 2001

(86) PCT No.: PCT/EP01/12965

§ 371 (c)(1),
(2), (4) Date: Sep. 15, 2003

(87) PCT Pub. No.: WO02/42299

PCT Pub. Date: May 30, 2002

(30) Foreign Application Priority Data

Nov. 22, 2000 (DE) .......................... 100 57 752
May 11, 2001 (DE) .......................... 101 22 895

(51) Int. Cl.$^7$ .................. C07D 471/04; A61K 31/437
(52) U.S. Cl. ..................... 514/212.08; 514/234.2; 514/234.6; 514/256; 540/524; 544/122; 544/328
(58) Field of Search ................. 544/122, 328; 540/524; 514/234.2, 256, 234.6, 212.08

(56) References Cited

U.S. PATENT DOCUMENTS

| 6,166,027 A | 12/2000 | Straub et al. | 514/269 |
| 6,180,656 B1 | 1/2001 | Furstner et al. | 514/406 |
| 6,451,805 B1 | 9/2002 | Straub et al. | 514/269 |

FOREIGN PATENT DOCUMENTS

| WO | 9816223 | 4/1998 |
| WO | 9816507 | 4/1998 |
| WO | 9823619 | 6/1998 |
| WO | 0006567 | 2/2000 |
| WO | 0006568 | 2/2000 |
| WO | 0006569 | 2/2000 |
| WO | 0021954 | 4/2000 |

OTHER PUBLICATIONS

Fisker et al., PubMed Abstract (J Endocrinol Invest. 22(5 Suppl):89–93), 1999.*
Layzer, Degenerative Diseases of the Nervous Sytem, Cecil Textbook of Medicine, 20$^{th}$ Edition, vol. 2, pp. 2050–7, 1996.*
Damasio, Alzheimer's Disease and Related Dementias, Cecil Textbook of Medicine, 20$^{th}$ Edition, vol. 2, pp. 1992–6, 1996.*
Ko., et al., Blood, *84*, 4226–4233 (1994).
Mulsch, et al., Br. J. Pharmacol. *120*, 681–689 (1997).
Pettibone, et al., Eur. J. Pharmacol. *116*, 307–312 (1985).
Yu, et al., Brit. J. Pharmacol. *114*, 1587–1594 (1995).

* cited by examiner

Primary Examiner—Deepak Rao

(57) ABSTRACT

The invention relates to novel pyrazolopyridine derivatives of formula (I)

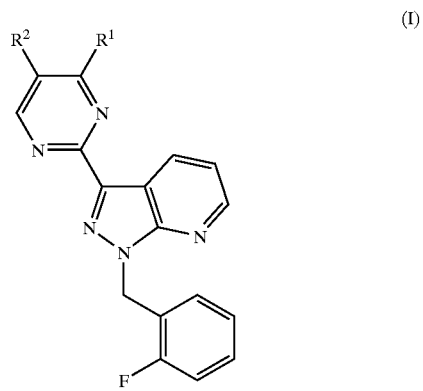

(I)

wherein $R^1$ represents $NH_2$ or $NHCO-C_{1-6}$-alkyl, and $R^2$ represents a radical of formula $R^3NCOR^4$ which is bonded to the remainder of the molecule by means of the nitrogen atom, $R^3$ and $R^4$ forming, together with the amide group to which they are bonded, a five to seven-membered heterocycle which may be saturated or partially unsaturated, may optionally contain a further heteroatom selected from the group N, O, and S and may comprise between one and five other substituents chosen from oxo, $C_{1-6}$alkyl, hydroxyl, hydroxy-$C_{1-6}$-alkyl, halogen, or may be fused to a $C_{6-10}$ aryl ring or a $C_{3-8}$ cycloalkyl ring in which optionally two carbon atoms are bonded to each other by means of an oxygen atom. The invention also relates to salts, isomers and hydrates of the derivatives in the form of stimulators of soluble guanylate cyclase and as agents for treating cardiovascular diseases, hypertonia, thrombo-embolic diseases and ischaemia, sexual dysfunction, inflammations, and diseases of the central nervous system. Processes for preparing these materials, and pharmaceutical compositions containing them are also disclosed and claimed.

18 Claims, No Drawings

LACTAM-SUBSTITUTED PYRAZOLOPYRIDINE DERIVATIVES

The present invention relates to novel chemical compounds which stimulate soluble guanylate cyclase, to the preparation thereof and to the use thereof as medicaments, in particular as medicaments for the treatment of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of CGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke, and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569 and WO 00/21954 describe pyrazolopyridine derivatves as stimulators of soluble guanylate cyclase. Also described in these patent applications are pyrazolopyridines having a pyrimidine residue in position 3. Compounds of this type have very high in vitro activity in relation to stimulating soluble guanylate cyclase. However, it has emerged that these compounds have some disadvantages in respect of their in vivo properties such as, for example, their behavior in the liver, their pharmacokinetic behavior, their dose-response relation or their metabolic pathway.

It was therefore the object of the present invention to provide further pyrazolopyridine derivatives which act as stimulators of soluble guanylate cyclase but do not have the disadvantages, detailed above, of the compounds from the prior art.

This object is achieved according to the present inventions by the compounds as claimed in claim 1. These novel pyrazolopyridine derivatives are distinguished by a pyrimidine residue in position 3, which has a particular substitution pattern, namely a cyclic lactam residue in position 5 of the pyrimidine ring and, where appropriate, an amino gmup in position 4 of the pyrimidine ring.

The present invention specifically relates to compounds of the formula (I)

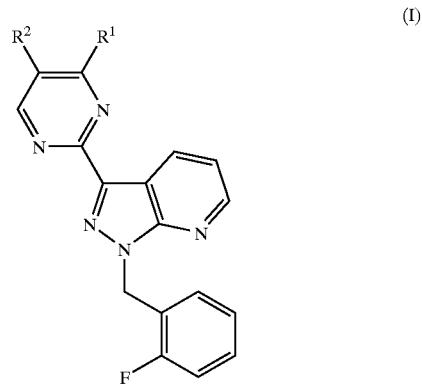

in which
$R^1$ is $NH_2$ or is NHCO—$C_{1-6}$-alkyl;
$R^2$ is a radical of the formula $R^3NCOR^4$ which is bonded via the nitrogen atom to the remainder of the molecule,
where
$R^3$ and $R^4$ together with the amide group to which they are bonded form a five- to seven-membered heterocycle which may be saturated or partially unsaturated, may optionally contain a further heteroatom from the group of N, O, S, and may have 1 to 5 further substituents from the group of oxo, $C_{1-6}$-alkyl, hydroxyl, hydroxy-$C_{1-6}$-alkyl, halogen, and may be fused to a $C_{6-10}$-aryl ring or to a $C_{3-8}$-cycloalkyl ring in which two carbon atoms are optionally connected together via an oxygen atom;

and salts, isomers and hydrates thereof.

According to an alternative embodiment, the present invention relates to compounds of the formula (I) in which
$R^1$ is $NH_2$ or is NHCO—$C_{1-6}$-alkyl;
$R^2$ is a radical of the formula $R^3NCOR^4$ which is bonded via the nitrogen atom to the remainder of the molecule,
where
$R^3$ and $R^4$ together with the amide group to which they are bonded form a saturated five- to seven-membered heterocycle which may optionally contain a further heteroatom from the group of N, O, S, and may have 1 to 5 further substituents from the group of oxo, $C_{1-4}$-alkyl, hydroxyl, hydroxy-$C_{1-4}$-alkyl, halogen, and may be fused to a $C_{6-10}$aryl ring or to a $C_{3-8}$-cycloalkyl ring in which two carbon atoms are optionally connected together via an oxygen atom;

and salts, isomers and hydrates thereof.

According to a further alternative embodiment, the present invention relates to compounds of the formula (I) in which $R^1$ is $NH_2$ or is $NHCOCH_3$;
$R^2$ is a radical of the formula $R^3NCOR^4$ which is bonded via the nitrogen atom to the remainder of the molecule, where $R^3$ and $R^4$ together with the amide group to which they are bonded form a saturated five- to seven-membered heterocycle which may optionally contain a further heteroatom from the group of N, O, S, and may have 1 to 5 further substituents from the group of oxo, $C_{1-4}$-alkyl, and may be fused to a phenyl ring or to a $C_{3-8}$-cycloalkyl ring in which optionally two carbon atoms are connected together via an oxygen atom;

and salts, isomers and hydrates thereof.

According to a further embodiment, the present invention relates to compounds of the formula (I) in which $R^1$ is $NH_2$;
$R^2$ is a radical of the formula $R^3NCOR^4$ which is bonded via the nitrogen atom to the remainder of the molecule, where $R^3$ and $R^4$ together with the amide group to which they are bonded form a five- to seven-membered heterocycle which may be saturated or partially unsaturated, may optionally contain a further heteroatom from the group of N, O, S, and may have 1 to 5 further substituents from the group of oxo, $C_{1-6}$-alkyl, hydroxyl, hydroxy-$C_{1-6}$alkyl, halogen, and may be fused to a $C_{6-10}$-aryl ring;

and salts, isomers and hydrates thereof.

According to a further embodiment, the present invention relates to compounds of the formula (I) in which $R^1$ is $NH_2$;
$R^2$ is a radical of the formula $R^3NCOR^4$ which is bonded via the nitrogen atom to the remainder of the molecule, where $R^3$ and $R^4$ together with the amide group to which they are bonded form a saturated five- to seven-membered heterocycle [lacuna] may optionally contain a further oxygen atom and may have 1 to 5 further substituents from the group of oxo, $C_{1-4}$-alkyl, hydroxyl, hydroxy-$C_{1-4}$-alkyl, F, and may be fused to a $C_{6-10}$-aryl ring;

and salts, isomers and hydrates thereof.

According to a further embodiment, the present invention relates to compounds of the formula (I) in which $R^1$ is $NH_2$;
$R^2$ is a radical of the formula $R^3NCOR^4$ which is bonded via the nitrogen atom to the remainder of the molecule, where $R^3$ and $R^4$ together with the amide group to which they are bonded form a five- or six-membered saturated heterocycle which may optionally contain a further oxygen atom and may have 1 to 5 further substituents from the group of oxo, $C_{1-4}$-alkyl, and may be fused to a phenyl ring;

and salts, isomers and hydrates thereof.

The compounds of the invention of the general formula (I) may also exist in the form of their salts. Salts which may generally be mentioned here are those with organic or inorganic bases or acids.

For the purposes of the present invention, physiologically acceptable salts are preferred. Physiologically acceptable salts of the compounds of the invention may be salts of the substances of the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds of the invention which have a free carboxyl group. Particularly preferred examples are sodium, potassium, magnesium or calcium salts, and ammonium salts derived from ammonia or organic amines such as, for example, ethylamine, di- or triethylamine, di- or triethanolamine, dicyclohexylamine, dimethylaminoethanol, arginine, lysine or ethylenediamine.

The compounds of the invention may exist in stereoisomeric forms which either are related as image and mirror image (enantiomers) or which are not related as image and mirror image (diastereomers). The invention relates both to the enantiomers or diastereomers and to the mixtures thereof in each case. The racemic forms can, just like the diastereomers, be separated in a known manner, for example by chromatographic separation, into the stereoisomerically pure constituents. Double bonds present in the compounds of the invention may be in the cis or trans configuration (Z or E form).

Certain compounds may moreover exist in tautomeric forms. This is known to the skilled worker, and the scope of the invention likewise covers such compounds.

The compounds of the invention may additionally occur in the form of their hydrates, where the number of water molecules bound to the molecule depends on the particular compound of the invention.

Unless otherwise indicated, for the purposes of the present invention the substituents generally have the following meaning:

Alkyl is generally a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodeyl, eicosyl.

Alkylene is generally a straight-chain or branched hydrocarbon bridge having 1 to 20 carbon atoms. Examples which may be mentioned are methylene, ethylene, propylene, -methylethylene, -methylethylene, -ethylethylene, -ethylethylene, butylene, -methylpropylene, -methylpropylene, -methylpropylene, ethylpropylene, ethylpropylene, -ethylpropylene, pentylene, hexylene, heptylene, octylene, nonylene, decylene, dodeylene and eicosylene.

Alkenyl is generally a straight-chain or branched hydrocarbon radical having 2 to 20 carbon atoms and one or more, preferably having one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkynyl is generally a straight-chain or branched hydrocarbon radical having 2 to 20 carbon atoms and one or more, preferably having one or two, triple bonds. Examples which may be named are ethynyl, 2-butynyl, 2-pentynyl and 2-hexynyl.

Acyl is generally straight-chain or branched lower alkyl having 1 to 9 carbon atoms bonded via a carbonyl group. Examples which may be mentioned are: acetyl, ethylcarbonyl, propylcarbonyl, isopropylcarbonyl, butylcarbonyl and isobutylcarbonyl.

Alkoxy is generally a straight-chain or branched hydrocarbon radical having 1 to 14 carbon atoms which is bonded via an oxygen atom. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy. The terms "alkoxy" and "alkyloxy" are used synonomously.

Alkoxyalkyl is generally an alkyl radical having up to 8 carbon atoms which is substituted by an alkoxy radical having up to 8 carbon atoms.

Alkoxycarbonyl can be represented for example by the formula

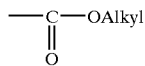

In this case, alkyl is generally a straight-chain or branched hydrocarbon radical having 1 to 13 carbon atoms. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Cycloalkyl is generally a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Cycloalkoxy is for the purposes of the invention an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonomously.

Aryl is generally an aromatic radical having 6 to 10 carbon atoms. Preferred aryl radicals are phenyl and naphthyl.

Halogen is for the purposes of the invention fluorine, chlorine, bromine and iodine.

Heterocycle is for the purposes of the invention generally a saturated, unsaturated or aromatic 3- to 10-membered, for example 5- or 6-membered, heterocycle which may comprise up to 3 heteroatoms from the series of S, N and/or O and which in the case of a nitrogen atom may also be bonded via the latter. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3 triazolyl, thiazolyl, oxazolyl, imidazolyl, morpholinyl or piperidyl. Thiazolyl, furyl, oxazolyl, pyrazolyl, triazolyl, pyridyl, pyrimidinyl, pyridazinyl and tetrahydropyranyl are preferred. The term "heteroaryl" (or "hetaryl") stands for an aromatic heterocyclic radical.

The compounds of the invention of the formula (I) can be prepared by

[A] reacting the compound of the formula (II)

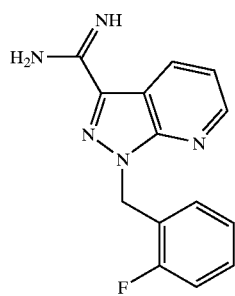

with compounds of the formula (III)

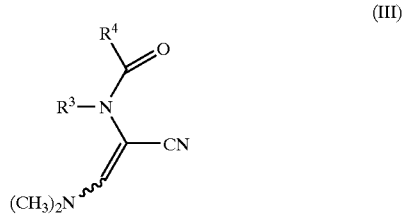

or with compounds of the formula (IV)

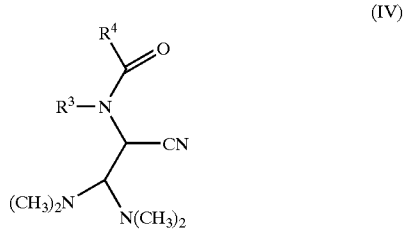

or with compoundsof the formula (V)

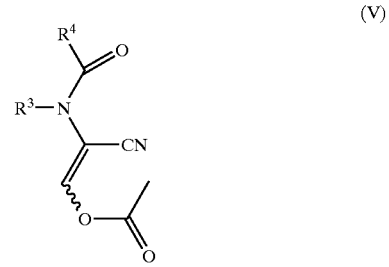

in which $R^3$ and $R^4$ have the meaning indicated above, in an organic solvent where appropriate in the presence of a base with heating to give compounds of the formula (I).

The compound of the formula (II) can be prepared as shown in the following reaction scheme:

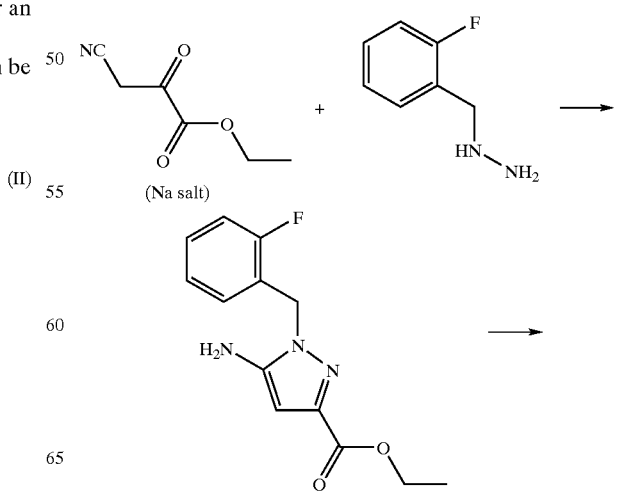

-continued

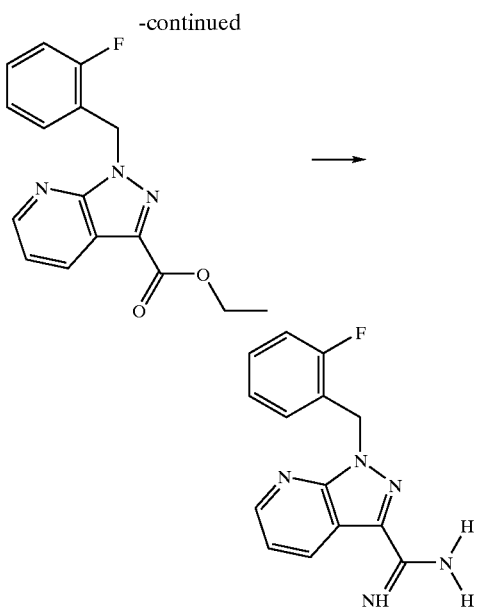

The compound of the formula (II) can be obtained in a multistage synthesis from the sodium salt of ethyl cyanopyruvate which is known from the literature (Borsche and Manteuffel, Liebigs. Ann. Chem. 1934, 512, 97). Reaction thereof with 2-fluorobenzylhydrazine with heating and under a protective gas atmosphere in an inert solvent such as dioxane results in ethyl 5-amino-1-(2-fluorobenzyl) pyrazole-3-carboxylate, which cyclizes to the corresponding pyridine derivative by reaction with dimethylaminoacrolein in acidic medium under a protective gas atmosphere and with heating. This pyridine derivative ethyl 1-(2-fluorobenzyl)-1H-pyrazolo[3,4-b]pyridine-3-carboxylate is converted by a multistage sequence consisting of conversion of the ester with ammonia into the corresponding amide, dehydration with a dehydrating agent such as trifluoroacetic anhydride to give the corresponding nitrile derivative, reaction of the nitrile derivative with sodium ethoxide and final reaction with ammonium chloride into the compound of the formula (II).

The compounds of the formulae (III) and (IV) can be prepared from the corresponding lactam derivatives of the formula (VIII)

(VIII)

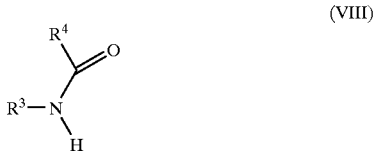

by reaction with a haloacetonitrile such as, for example, bromoacetonitrile, employing the acetonitrile derivative in equimolar amount or in slight excess, in the presence of an equimolar amount or of a slight excess of a base such as, for example, an alkali metal hydride, in particular sodium hydride, in an organic solvent such as, for example, a cyclic ether, in particular dioxane, or preferably in a mixture of organic solvents such as, in particular, a mixture of dioxane and dimethylformamide (DMF) in the ratio 3:1 to 5:1, where appropriate in the presence of an equimolar amount or of a slight excess of a lithium compound such as lithium bromide, preferably under atmospheric pressure, mixing the reactants while cooling to, for example, −5° C. to +5° C. and subsequently stirring the reaction solution for several hours, for example 12 hours, at elevated temperature, for example 50–80° C., preferably 60–70° C., to give the compounds of the formula (IX)

(IX)

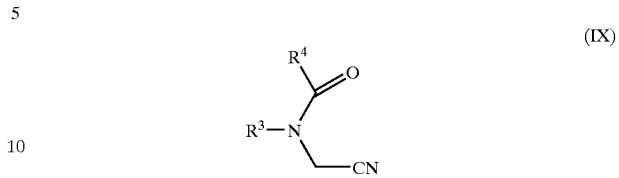

and subsequently reacting the compounds of the formula (IX) with an equimolar amount or of a slight excess of t-butoxybis(dimethylamino)methane (can be purchased for example from Aldrich) in an organic solvent such as, for example, a cyclic ether, in particular dioxane, preferably under atmospheric pressure and stirring the reaction solution for several hours, for example 12 hours, at elevated temperature, for example 50–80° C., preferably 60–70° C.

The compounds of the formula (VIII) can be obtained for example from Aldrich or Fluka (-butyrolactam, -valerolactam, -caprolactam, 5-methyl-2-pyrrolidinone, oxazolidin-2-one, 5,5-dimethyl-1,3oxazolidine-2,4-dione, 3-methyl-2-pyrrolidinone) or can be prepared by literature methods. For example, 5,5-dimethylpyrrolidin-2-one can be synthesized as described in J. Org. Chem., 14, 1949, 605–625, J. Heterocycl. Chem. 23, 1986, 53–57 or Tetrahedron Lett., 35, 1994, 293–296. The preparation of 3-morpholinone is described for example in the patents U.S. Pat. Nos. 5,349,045, 3,966,766 and 4,156,683 and in J. Amer. Chem. Soc. 61; 1939; 1575. 3,3,4,4-Tetramethylpyrrolidin-2-one can be prepared as described in Justus Liebigs Ann. Chem. 1977; 8–19. Substituted 3-morpholinones can be prepared by reaction of -chloro carbonyl chlorides with substituted 2-aminoethanols as described in Tetrahedron lett. 1995, 36, 3821–3824. 4,4-Dimethyl-1,3-oxazolidin-2-one can be prepared from 2-amino-2-methylpropanol and diethyl carbonate as described in Tetrahedron, 47, 1991, 2801–2820.

The compounds of the formula (V) can be obtained from the compounds of the formula (IX) by reaction with an excess, for example a 2- to 3-fold excess, of a formic acid derivative such as, for example, a formic ester such as ethyl formate in an organic solvent, such as, for example, a cyclic ether, preferably tetrahydrofuran (THF), in the presence of an excess, for example a 2- to 3-fold excess, of a base, for example of an alkali metal base, preferably KOtBu, preferably under atmospheric pressure and stirring the reaction solution for several hours, for example 1 to 2 hours, at room temperature, and subsequently reacting with an amount of acetic acid corresponding to the amount of base employed, and subsequently reacting with an acetic acid derivative such as acetyl chloride or acetic anhydride with cooling and subsequently stirring preferably under atmospheric pressure for a few minutes up to several hours, for example 30 minutes to 2 hours, at room temperature.

The compounds of the formula (II) can be reacted with compounds of the formula (III) or (IV) or (V) in an organic solvent such as, for example, a hydrocarbon, preferably an aromatic hydrocarbon, in particular xylene or toluene, where appropriate in the presence of a base, for example an organic base such as an amine, preferably triethylamine, preferably under atmospheric pressure and stirring the reaction solution for several hours, for example 12 hours, at elevated temperature, for example 80–130° C., preferably 100–130° C., in particular 120° C., to give the compounds of the invention of the formula (I). The reactants can in this case, depending on their nature, be employed in equimolar amounts, or one of the reactants is employed in an up to three-fold excess.

The compounds of the invention of the general formula (I) show a valuable range of pharmacological effects which could not be predicted.

The compounds according to the invention of the general formula (I) bring about vasorelaxation and an inhibition of platelet aggregation and lead to a reduction in blood pressure and an increase in coronary blood flow. These effects are mediated by direct stimulation of soluble guanylate cyclase and an intracellular increase in cGMP. In addition, the compounds according to the invention of the general formula (I) enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transistorily and ischemic attacks, disturbances of peripheral blood flow, prevention of restenoses as after thrombolysis therapies, percutaneously transluminal angioplasties (PTAs), percutaneously transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, osteoporosis, gastroparesis and incontinence.

The compounds described in the present invention of the general formula (I) also represent active ingredients for controlling central nervous system diseases. characterized by disturbances of the NO/cGMP system. They are suitable in. particular for improving perception, concentration, learning or memory after cognitive impairments like those occurring in particular in association with situations/diseases/ syndromes such as mild cognitive impairment, age-associated learning and memory impairments, age-associated memory loss, vascular dementia, craniocerebral trauma, stroke, dementia occurring after strokes (post stroke dementia), post-traumatic cranial cerebral trauma, general concentration impairments, concentration impairments in children with learning and memory problems, Alzheimer's disease, vascular dementia, lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The active ingredients are furthermore also suitable for controlling cerebral blood flow and thus represent effective agents for controlling migraine.

They are also suitable for the prophylaxis and control of the sequelae of cerebral infarctions such as stroke, cerebral ischemeias and craniocerebral trauma. The compounds of the invention of the general formula (I) can likewise be employed for controlling states of pain.

In addition, the compounds of the invention have an anti-inflammatory effect and can therefore be employed as anti-inflammatory agents.

Furthermore, the invention encompasses the combination of the compounds of the invention of the general formula (I) with organic nitrates and NO donors.

Organic nitrates and NO donors for the purposes of the invention are generally substances which display their therapeutic effect via release of NO or NO species. Preference is given to sodium nitroprusside, nitroglycerine, isosorbide dinitrate, isosorbide mononitrate, molsidomine and SIN-1.

In addition, the invention encompasses the combination with compounds which inhibit breakdown of cyclic guanosine monophosphate (cGMP). These are in particular inhibitors of phosphodiesterases 1, 2 and 5; nomenclature of Beavo and Reifsnyder (1990), TiPS 11 pp. 150 to 155. These inhibitors potentiate the effect of the compound of the invention, and the desired pharmacological effect is increased.

Biological Investigations
Vasorelaxant Effect in vitro

Rabbits are stunned by a blow to the back of the neck and are exsanguinated. The aorta is removed, freed of adherent tissue, divided into rings 1.5 mm wide and put singly under tension in 5 ml organ baths containing carbogen-gassed Krebs-Henseleit solution at 37° C. with the following composition (mM): NaCl: 119; KCl: 4.8; $CaCl_2 \times 2H_2O$: 1; $MgSO_4 \times 7\ H_2O$: 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated is investigated in each further run in increing dosage in each case, and the height of the contraction is compared with the height of the contraction reached in the last preceding run. The concentration necessary to reduce the height of the control value by 50% ($IC_{50}$) is calculated from this. The standard application volume is 5 µl, and the DMSO content in the bath solution corresponds to 0.1%. The results are listed in Table 1 below:

TABLE 1

| Vasorelaxant effect in vitro | |
|---|---|
| Example No. | $IC_{50}$ [µM] |
| 2 | 1.1 |
| 3 | 1.99 |
| 5 | 1.05 |
| 9 | 0.70 |
| 13 | 0.69 |
| 14 | 0.42 |
| 15 | 1.2 |
| 16 | 1.23 |
| 19 | 0.41 |
| 21 | 0.25 |
| 22 | 0.60 |

Determination of the Liver Clearance in vitro

Rats are anethstized, heparinized, and the liver is purfused in situ via the portal vein. Primary rat hepatocytes are then obtained ex vivo from the liver using collagenase solution. $2.10^6$ hepatocytes per ml were incubated at 37° C. with the same concentration in each case of the compound to be investigated. The decrease of the substrate to be investigated over time was determined bioanalytically (HPLC/UV, HPLC/fluoroscene or LC/MSMS) at 5 points in time in each case in the period from 0–15 min after the start of incubation. From this, the clearance was calculated by means of the cell count and liver weight.

The substance to be investigated is administered as a solution intravenously to rats via the tail vein. At fixed points in time, blood is taken from the rats, heparinized and plasma is obtained therefrom by conventional measures. The substance is quantified bioanalytically in the plasma. The pharmacokinetic parameters are calculated from the plasma concentration-time courses determined in this way by means of conventional non-compartmental methods used for this purpose.

The present invention includes pharmaceutical preparations which, besides nontoxic, inert pharmaceutically suitable carriers, comprises the compounds of the invention of the general formula (I), and processes for producing these preparations.

The active ingredient may be present where appropriate in one or more of the carriers indicated above also in mnicroencapsulated form.

The therapeutically effective compounds of the general formula (I) ought to be present in the pharmaceutical preparations mentioned above in a concentration of about 0.1 to 99.5, preferably of about 0.5 to 95, % by weight of the complete mixture.

The pharmaceutical preparations mentioned above may, apart from the compounds of the invention of the general formula (I), also comprise other active pharmaceutical ingredients.

It has generally proved advantageous both in human and in veterinary medicine to administer the active ingredient(s) of the invention in total amounts of about 0.01 to about 700, preferably 0.01 to 100, mgtkg of body weight per 24 hours, where appropriate in the form of a plurality of single doses, to achieve the desired results. A single dose comprises the active ingredient(s) of the invention preferably in amounts of about 0.1 to about 80, in particular 0.1 to 30, mg/kg of body weight.

The present invention is described in more detail below by means of non-restrictive preferred examples. Unless indicated elsewhere, all quantitative data relate to percentages by weight.

EXAMPLES

Abbreviations:
RT: room temperature
EA: ethyl acetate
DMF: N,N-dimethylformamide
Methods for Establishing the HPLC Retention Times, and Preparative Separation Methods:
Method A (HPLC-MS):
Eluent: A=$CH_3CN$ B=0.6 g 30% HCl/l $H_2O$
Flow rate: 0.6 ml/min
Column oven: 50° C.
Column: symmetry C18 2.1*150 mm
Gradient:

| Time (min) | % A | % B | Flow rate (ml/min) |
|---|---|---|---|
| 0 | 10 | 90 | 0.6 |
| 4 | 90 | 10 | 0.6 |
| 9 | 90 | 10 | 0.8 |

Method B (HPLC):
Eluent: A=5 ml $HClO_4$/l $H_2O$, B=$CH_3CN$
Flow rate: 0.75 ml/min
L-R temperature: 30.00° C. 29.99° C.
Column: Kromasil C18 60*2 mm
Gradient:

| Time (min) | % A | % B |
|---|---|---|
| 0.50 | 98 | 2 |
| 4.50 | 10 | 90 |
| 6.50 | 10 | 90 |
| 6.70 | 98 | 2 |
| 7.50 | 98 | 2 |

Method C (HPLC):
Eluent: A=$H_3PO_4$ 0.01 mol/l, B=$CH_3CN$
Flow rate: 0.75 ml/min
L-R temperature: 30.01° C. 29.98° C.
Column: Kromasil C18 60*2 mm
Gradient:

| Time (min) | % A | % B |
|---|---|---|
| 0.00 | 90 | 10 |
| 0.50 | 90 | 10 |
| 4.50 | 10 | 90 |
| 8.00 | 10 | 90 |
| 8.50 | 90 | 10 |
| 10.00 | 90 | 10 |

Method D (chiral HPLC):
Eluent: 50% isohexane, 50% ethanol
Flow rate: 1.00 ml/min
Temperature: 40° C.
Column: 250*4.6 mm, packed with Chiralcel OD, 10 μm
Method E (MPLC-MS):
Eluent: A=$CH_3CN$ B=0.3 g 30% HCl/l $H_2O$
Flow rate: 0.9 ml/min
Column oven: 50° C.
Column: Symmetry C18 2.1*150 mm
Gradient:

| Time (min) | % A | % B | Flow rate (ml/min) |
|---|---|---|---|
| 0 | 10 | 90 | 0.9 |
| 3 | 90 | 10 | 1.2 |
| 6 | 90 | 10 | 1.2 |

Method F (preparative HPLC):
Eluent: A=milli-Q water, B=acetonitrile, C=1% trifluoroacetic acid
Flow rate: 25 ml/min
Temperature: 50° C.
Packing material: Kromasil 100 C18 5 μm 250×20 mm No. 1011314R

| Time (min) | A | B | C |
|---|---|---|---|
| 0 | 72 | 10 | 18 |
| 30 | 32 | 60 | 8 |
| 30.1 | 4 | 95 | 1 |
| 40 | 4 | 95 | 1 |
| 48 | 72 | 10 | 18 |

Method G=(LC-MS):
Eluent: A=acetonitrile+0.1% formic acid, B=water+0.1% formic acid Flow rate: 25 ml/min
Temperature: 40° C.
Packing material: Symmetry C18, 50×2.1 mm, 3.5 μm

| Time (min) | A | B |
|---|---|---|
| 0 | 10 | 90 |
| 4.0 | 90 | 10 |
| 6.0 | 90 | 10 |
| 6.1 | 10 | 90 |
| 7.5 | 10 | 90 |

Method H (GC-MS):
Carrier gas: Helium
Flow rate: 1.5 ml/min
Initial temperaure: 60° C.
Temperature gradient: 14° C./min to 300° C., then 1 min const. 300° C.
Column: HP-5 30 m×320 μm×0.25 μm (film thickness)
Initial time: 2 min
Front injector temp.: 250° C.
Starting Compounds:

I. Synthesis of Lactam-substituted Acetonitriles

Example Ia (3-oxo-4-morpholinyl)acetonitrile

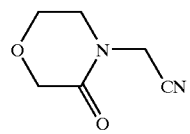

3.01 g (126 mmol) of sodium hydride were added in portions to 12.1 g (120 mmol) of morpholinone in a mixture of 150 ml of dioxane and 30 ml of DMF while cooling in ice, and the mixture was stirred at 0° C. for 40 min. Then 11.4 g (132 mmol) of anhydrous lithium bromide were added and the mixture was stirred at RT for 30 min. Dropwise addition of 15.8 g (132 mmol) of bromoacetonitrile was followed by stirring at 65° C. overnight. The suspension was cooled to RT and poured into saturated NaCl solution. Extraction with ethyl acetate, drying of the organic phase over sodium sulfate and removal of the solvent by distillation in a rotary evaporator and chromatography of the residue on silica gel with dichloromethane/methanol 30:1 afforded product which still contained 33% DMF and which was employed in the next reaction without further purification.

Yield: 13.0 g (52%, free of DMF content).

$^1$H-NMR: (300 MHz, $D_6$-DMSO), δ=3.45 (t, 2H, $CH_2$N), 3.88 (t, 2H $CH_2$O), 4.12 (s, 2H, $CH_2$O), 4.48 (s, 2H, $CH_2$CN).

MS: (ESI pos.), m/z=141 ([M+H]$^+$), 182 ([M+H+$CH_3$CN]$^+$).

The following were prepared in an analogous way from the appropriate lactams or from the appropriate cyclic carbamates by reaction with bromoacetonitrile:

| Ex. | Formula | Yield (%) | Spectroscopic data |
|---|---|---|---|
| Ib | | 23 (a) | MS-ESI pos. (m/z): 166 [M + H + $CH_3$CN]$^+$ Rf($CH_2Cl_2$/MeOH 10:1): 0.57 |
| Ic | | 34 | MS-ESI pos. (m/z): 139 [M + H]$^+$, 180 [M + H + $CH_3$CN]$^+$ Rf($CH_2Cl_2$/MeOH 10:1): 0.61 |
| Id | | 39 (b) | MS-ESI pos. (m/z): 139 [M + H]$^+$, 156 [M + H + $NH_3$]$^+$ Rf($CH_2Cl_2$/MeOH 10:1): 0.56 |
| Ie | | 32 | MS-ESI pos. (m/z): 153 [M + H]$^+$, 194 [M + H + $CH_3$CN]$^+$ |
| If | | 58 | MS-ESI pos. (m/z): 153 [M + H]$^+$, 170 [M + H + $NH_3$]$^+$ Rf($CH_2Cl_2$/MeOH 10:1): 0.56 |
| Ig | | 27 | MS-CI pos. (m/z): 170 ([M + H]+), 187 ([M + H + $NH_3$]$^+$) $^1$H-NMR (200 MHz, $d^6$-DMSO): δ = 0.88(s, 6H, 2$CH_3$), 0.95(s, 6H, 2$CH_3$), 3.12(s, 2H, $CH_2$), 4.38(s, 2H, $CH_2$CN) |
| Ih | | 33 | MS-CI pos. (m/z): 139 ([M + H]$^+$), 156 ([M + H + $NH_3$]$^+$) $^1$H-NMR (200 MHz, $d^6$-DMSO): δ = 1.06(d, 3H, $CH_3$), 1.50–1.70(m, 1H, CH), 2.13–2.45(m, 2H, 2CH), 3.28–3.40(m, 2H, 2CH), 4.36(s, 2H, $CH_2$CN) |
| Ii | | 30 | MS-DCI (m/z): 169.1 ([M + H]$^+$), 186.1 ([M + H + $NH_3$]$^+$), 354.4 ([2M + H + $NH_3$]+) $^1$H-NMR (200 MHz, $d^6$-DMSO): δ = 1.28(s, 6H, 2$CH_3$), 3.62(s, 2H, $CH_2$N), 4.16(s, 2H, $CH_2$O), 4.40(s, 2H, $CH_2$CN) |
| Ij | | 14 | MS-CI pos. (m/z): 172 ([M + H + $NH_3$]$^+$) $^1$H-NMR (200 MHz, $d^6$-DMSO): δ = 1.31(s, 6H, 2$CH_3$), 4.10(s, 2H, $CH_2$), 4.35(s, 2H, $CH_2$CN) |

-continued

| Ex. | Formula | Yield (%) | Spectroscopic data |
|---|---|---|---|
| Ik | | 39 | $R_f$: 0.55($CH_2Cl_2$/MeOH 20:1)<br>HPLC: $R_f$ = 1.59 min (Method B). |
| Il | | 65 | $R_f$: 0.60($CH_2Cl_2$/MeOH 20:1)<br>HPLC: $R_f$ = 2.57 min (18%) and 2.66 min (80%), mixture of diastereomers, (Method B). |
| Im | | 55 | $R_f$: 0.51($CH_2Cl_2$/MeOH 20:1)<br>GC-MS: $R_t$ = 8.84 min (Method H).<br>MS (TOF-EI), m/z = 125 ([M − $C_3H_7$]+. |

(a) The reaction was carried out in dimethoxymethane/DMF 5:1
(b) Racemate

II. Synthesis of Lactam-substituted Acrylonitriles and Propionitriles

Example IIa
3-(Dimethylamino)-2-(3-oxo-4-morpholinyl)-2-propenonitrile (E/Z mixture)

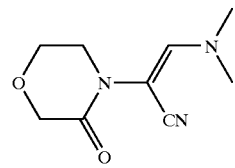

16.2 g (19.2 ml, 92.8 mmol) of tert-butoxybis(dimethylamino)methane were added to a solution of 13.0 g (67% strength in DMF, 62.2 mmol) of (3-oxo-4-morpholinyl)acetonitrile from Exp. Ia in 150 ml of dioxane at room temperature, and the mixture was then stirred at 80° C. overnight. The residue remaining after the solvent had been stripped off in a rotary evaporator was chromatographed on silica gel with dichloromethane/methanol 20:1. A brown oil was obtained, from which product crystallized. After treatment with methanol in an ultrasonic bath, cyclohexane was added in order to precipitate the product as pale brown solid. The product is, according to the NMR spectrum (300 MHz, $D_6$-DMSO), in the form of an E/Z mixture.
Yield: 10.2 g (84%).
$^1$H-NMR: (200 MHz, $D_6$-DMSO), δ=2.88 and 3.03 (2s, together 6H, N($CH_3$)$_2$), 3.38–3.52 (m, 2H, $CH_2N$), 3.80–3.91 (m, 2H, $CH_2O$), 4.09 and 4.12 (2s, together 2H, $CH_2O$), 6.91 and 7.01 (2s, together 1H, olefin CH).
MS: (ESI pos.), m/z=196 ([M+H]+).
The following were obtained in an analogous way:

| Ex. | Formula | Yield (%) | Spectroscopic data |
|---|---|---|---|
| IIb (from Ib) | | 69 | MS-ESI pos. (m/z): 180 [M + H]+<br>Retention time (min) (Method A): 2.034 and 2.146 (E/Z mixture) |
| IIc (from Ic) | | 21 | MS-ESI pos. (m/z): 194 [M + H]+<br>Retention time (min) (Method A): 2.272 (E/Z mixture) |
| IId (from Id) | | 28 | MS-ESI pos. (m/z): 239 [M + H]+, 194 [M + H − $HNMe_2$]+[a]<br>Retention time (min) (Method A): 2.388 and 2.460 (2 diastereomers) |

-continued

| Ex. | Formula | Yield (%) | Spectroscopic data |
| --- | --- | --- | --- |
| IIe (from Ie) | | 31 | MS-ESI pos. (m/z): 208 [M + H]+ Retention time (min) (Method A): 2.521 and 2.598 (E/Z mixture) |
| IIf (from If) | | 45 | MS-ESI pos. (m/z): 208 [M + H]+, 415 [2 M + H]+, Retention time (min) (Method A): 1.819 and 1.869 (E/Z mixture) |
| IIg (from Ig) | | 61 | MS-ESI pos. (m/z): 236 ([M + H]+), 471 ([2M + H]+) Retention time (min) (Method A): 2.214 (peak with shoulder, E/Z mixture) |
| IIh (from Ih) | | 43 | MS-ESI pos. (m/z): 194 ([M + H]+), 387 ([2M + H]+) Retention time (min) (Method A): 1.626 and 1.685 (E/Z mixture) |
| IIi (from Ii) | | 32 | MS-ESI pos. (m/z): 224 ([M + H]+), 447 ([2M + H]+) Retention time (min) (Method A): 1.599 and 1.658 (E/Z mixture) |
| IIj (from Ij) | | 14 | MS-ESI pos. (m/z): 224 ([M + H]+), 447 ([2M + H]+) Retention time (min) (Method A): 1.599 and 1.658 (E/Z mixture) |

-continued

| Ex. | Formula | Yield (%) | Spectroscopic data |
|---|---|---|---|
| IIk (from Il) | | 4 | Reacted further as crude product |
| III (from Im) | | 21 | LC-MS: $R_t$ = 1.98 min (14%) and 2.05 min (78%), mixture of diastereomers (Method E). MS (ESI pos.), m/z = 224 ([M + H]$^+$, 447 ([2M + H]$^+$). |

[a] HNMe$_2$ elimination evidently occurs in the MS apparatus.

III. Synthesis of 3-(dimethylamino)(5,5-dimethyl-2,4dioxo-1,3oxazolidin-3-yl)-2-propenonitrile

III a) (5,5-Dimethyl-2,4-dioxo-1,3-oxazolidin-3-yl)acetonitrile

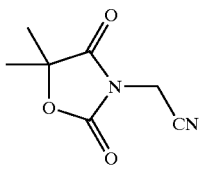

A solution of 10.0 g (77.5 mmol) of 5,5-dimethyloxazolidine-2.4-dione in 30 ml of DMF was added dropwise to a suspension of 3.25 g (81.3 mmol) of sodium hydride (60% in mineral oil) in 200 ml of dioxane while cooling in ice. The mixture was stirred for 40 min while warming to room temperature. Then 7.40 g (85.2 mmol) of anhydrous lithium bromide were added, and the mixture was stirred at RT for 20 min. Dropwise addition of 10.2 g (85.2 mmol) of bromoacetonitrile was followed by stirring at 65° C. overnight. The suspension was cooled to RT and poured into saturated NaCl solution. The organic phase was absorbed onto silica gel and chromatographed with dichloromethane/methanol 50:1. The product-containing fractions were dried under high vacuum for partial removal of the DMF still present. The product treated in this way still contained 44 mol % DMF and was employed without further purification in the next reaction.

Yield: 16.0 g (69%).

$^1$H-NMR: (300 MHz, D$_6$-DMSO), δ=1.52 (s, 6H, CH$_3$), 4.61 (s, 2H, CH$_2$CN).

$R_f$: 0.76 (dichloromethane/methanol 20:1).

III b) 3-(Dimethylamino)-(5,5-dimethyl-2,4-dioxo-1,3-oxazolidin-3-yl)-2-propenonitrile (E/Z mixture)

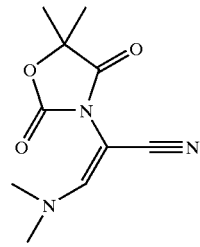

5.80 g (6.88 ml, 33.3 mmol) of tert-butoxybis(dimethylamino)methane were added to a solution of 10.0 g (56% strength in DMF, 33.3 mmol) of (5,5-dimethyl-2,4-dioxo-1,3-oxazolidin-3-yl)acetonitrile from Example III a in 150 ml of dioxane at room temperature, and the mixture was then stirred at 80° C. overnight. The mixture was absorbed onto silica gel and chromatographed with cyclohexane/ethyl acetate gradient (1:1, 1:2, 1:3). The productcontaining fractions were concentrated, taken up in ethyl acetate and precipitated with cyclohexane. The precipitate was filtered off with suction and washed with diethyl ether, resulting in a pale yellow solid. The product is, according to the NMR spectrum (300 MHz, D$_6$-DMSO), in the form of an E/Z mixture.

Yield: 2.44 g (57%).

$^1$H-NMR: (200 MHz, D$_6$-DMSO), δ=1.54 (s, 6H, CH$_3$), 3.11 and 3.32 (2s, together 6H, N(CH$_3$)$_2$), 7.27 and 7.37 (2s, together 1H, olefin CH).

MS: (ESI pos.), m/z=224 ([M+H]$^+$), 265 ([M+H+CH$_3$CN]$^+$).

IV. Synthesis of 3(dimethylamino)-2-(2oxo-1, 3oxazolidin-3-yl)2-propenonitrile

IV a) (2-Oxo-1,3-oxazolidin-3-yl)acetonitrile

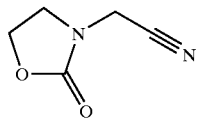

A solution of 15.0 g (172.3 mmol) of 2-oxazolidinone in 30 ml of DMN was added dropwise to a suspension of 7.23 g (180.9 mnmol) of sodium hydride (60% in mineral oil) in 200 ml of dioxane while cooling in ice. The mixture was stirred for 40 min, during which it warmed to room temperature. Then 16.5 g (189.5 mmol) of anhydrous lithium bromide were added, and the mixture was stirred at RT for 40 min. Dropwise addition of 22.7 g (189.5 mmol) of bromoacetonitlile was followed by stirring at 65° C. overnight. The suspension was cooled to RT and poured into saturated NaCl solution. The organic phase was absorbed onto silica gel and chromatographed with dichloromethane/methanol 50:1. The product-containing fractions were subjected to a further chromatography on silica gel using cyclohexane/ethyl acetate 1:1 as eluent.

Yield: 19.9 g (91%).

$^1$H-NMR: (300 MHz, $D_6$-DMSO), δ=3.61 (t, 2H, $CH_2N$), 4.35 (t, 2H, $CH_2O$), 4.39 (s, 2H, $CH_2CN$).

$R_f$: 0.56 (dichloromethane/methanol 20:1).

MS: (EI), mz (%)=126 (60, $M^+$), 67 (100).

IV b) 3-(Dimethylamino)2-(2-oxo-1,3-oxazolidin-3-yl)-2-propenonitrile (E/Z mixture)

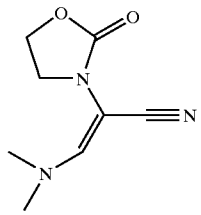

13.8 g (16.4 ml, 79.3 mmol) of tert-butoxybis(dimethylamino)methane was added to a solution of 10.0 g (79.3 mmol) of (2-oxo-1,3-oxazolidin-3-yl)acetonitrile from Ex. IV a in 200 ml of dioxane at room temperature, and the mixture was then stirred at 80° C. for 6 h and at room temperature overnight. The mixture was evaporated to dryness in a rotary evaporator and chromatographed on silica gel with cyclohexane/ethyl acetate gradient (1:1, 1:2, 1:3). The product is, according to the NMR spectrum (300 MHz, $D_6$-DMSO), in the form of an E/Z mixture.

Yield. 12.3 g (67%).

$^1$H-NMR: (200 MHz, $D_6$-DMSO), δ=2.94 and 3.03 (2s, together 6H, $N(CH_3)_2$), 3.58–3.68 (m, together 2H, $CH_2N$), 4.23–4.42 (m, together 2H, $CH_2O$), 6.97 and 7.13 (2s, together 1H, olefin CH).

MS: (DCI), m/z=182 ([M+H]$^+$), 199 ([M+H+$NH_3$]$^+$, 380 ([2M+H+$NH_3$]$^+$).

V. Synthesis of 1-(2-fluorobenzyl)1H-pyrazolo[3,4b]pyridine-3-carboxamidine

V a) Ethyl 5-amino-1-(2-fluorobenzyl)pyrazole-3-carboxylate

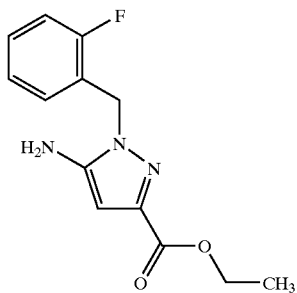

111.75 g (75 ml, 0.98 mol) of trifluoroacetic acid are added to 100 g (0.613 mol) of the sodium salt of ethyl cyanopyruvate (prepared in analogy to Borsche and Manteuffel, Liebigs Ann. 1934, 512, 97) while stirring efficiently in 2.5l of dioxane at room temperature under argon, and the mixture is stirred for 10 min, during which most of the precursor dissolves. Then 85.93 g (0.613 mol) of 2-fluorobenzylhydrazine are added, and the mixture is boiled overnight. After cooling, the sodium trifluoroacetate crystals which have separated out are filtered off with suction and washed with dioxane, and the crude solution is reacted further.

V b) Ethyl -(2-fluorobenyl)-1H-pyrazolo[3,4-b]pyridine-3-carboxylate

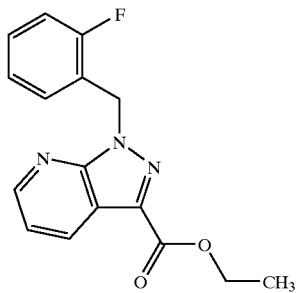

The solution obtained from V a) is mnixed with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, and the residue is poured into 2l of water and extracted three times with 1l of ethyl acetate each time. The combined organic phases are dried with magnesium sulfate and concentrated in a rotary evaporator. Chromatography is carried out on 2.5 kg of silica gel, eluting with a toluenetoluene-ethyl acetate=4:1 gradient. Yield: 91.6 g (49.9% of theory over two stages).

Melting point 85° C.

$R_f$(SiO$_2$, T1E1): 0.83.

V c) 1-(2-Fluorobenzyl)-1H-pyrazolo[3,4-b]pyridine-3-carboxamide

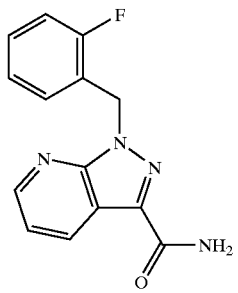

10.18 g (34 mmol) of the ester obtained in Example V b) are introduced into 150 ml of methanol saturated with ammonia at 0–10° C. Stirring at room temperature for two days is followed by concentration in vacuo.

$R_f$(SiO$_2$,T1E1): 0.33

V d) 3-Cyano-1-(2-fluorobenzyl)-1H-pyrazolo[3,4-b]pyridine

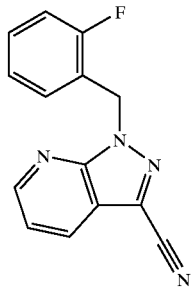

36.1 g (133 mmol) of 1-(2-fluorobenzyl)-1H-pyrazolo[3,4-b]pyridine-3-carboxamide from Example V c) are dissolved in 330 ml of THF, and 27 g (341 mmol) of pyridine are added. Then, over the course of 10 min, 47.76 ml (71.66 g, 341 mmol) of trifluoroacetic anhydride are added, during which the temperature rises to 40° C. The mixture is stirred at room temperature overnight. The mixture is then poured into 1 l of water and extracted three times with 0.5 l of ethyl acetate each time. The organic phase is washed with saturated sodium bicarbonate solution and with 1 N HCl, dried with MgSO$_4$ and concentrated in a rotary evaporator.

Yield: 33.7 g (100% of theory).

Melting point: 81° C.

$R_f$(SiO$_2$, T1E1): 0.74.

V e) Methyl (2-fluorobenzyl)-1H-pyrazolo[3,4-b]pyridine-3-carboximidate

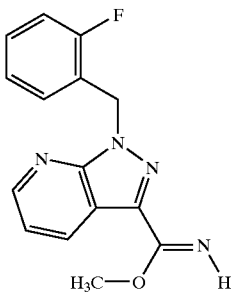

30.37 g (562 mmol) of sodium methoxide are dissolved in 1.5 l of methanol, and 36.45 g (144.5 mmol) of 3-cyano-1-(2-fluorobenzyl)-1H-pyrazolo[3,4-b]pyridine (from Example V d) are added. The solution obtained after stirring at room temperature for 2 hours is employed directly for the next stage.

V f) 1-(2-Fluorobenyl)-1H-pyrazolo[3,4-b]pyridine-3-carboxamidine

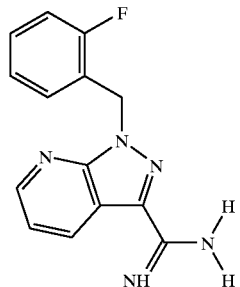

The solution of methyl (2-fluorobenzyl)-1H-pyrazolo[3,4-b]pyridine-3-carboximidate in methanol obtained from Example V e) is mixed with 33.76 g (32.19 ml, 562 mmol) of glacial acetic acid and 9.28 g (173 mmol) of ammonium chloride and stirred under reflux overnight. The solvent is evaporated in vacuo, the residue is thoroughly triturated with acetone, and the precipitated solid is filtered off with suction.

$^1$H-NMR (d$_6$-DMSO, 200MHz): δ=5.93 (s, 2H); 7.1–7.5 (m, 4H); 7.55 (dd, 1H); 8.12 (dd, 1H); 8.30 (dd, 1H); 9.5 (bs, 4H exchangeable) ppm.

MS (EI): m/z=270.2 (M-HCl).

VI. Synthesis of 2-cyano-1-(1,3-dioxo-1,3-dihydro-2H-isoindol-2-yl)ethenyl acetate

VI a) (1,3-Dioxo-1,3-dihydro-2H-isoindol-2-yl)acetonitrile

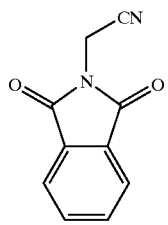

Phthalimide (1.35 g, 9.17 mmol, 1.1 equivalent) and potassium carbonate (5.76 g, 41.7 mmol, 5.0 equivalents) were suspended in DMF and, after 10 min, bromoacetonitrile (1.00 g, 8.34 mmol) was added. After stirring at room temperature for 2 h, the precipitate which had separated out was filtered off. The mother liquor was diluted with EA and extracted with saturated aqueous NaCl solution. The combined organic phases were concentrated in a rotary evaporator. 1.48 g (95%) of the desired compound were obtained in this way.

Yield: 1.48 g (95%).

$R_f$: 0.76 ($CH_2Cl_2$/MeOH 100/1).

$^1$H-NMR: (200 MHz, $D_6$-DMSO), δ=4.75 (s, 2H, $CH_2$), 7.8–8.0 (m, 4H, Ar-H).

MS: (DCI), m/z=204 ($[M+NH_4]^+$), 221 ($[M+N_2H_7]^+$), 390 ($[2M+NH_4]^+$).

MS: Retention time: 2.8 min (column: Symmetry, C-18, 3.5 μm, 50×2.1 mm, flow rate 0.5 ml/min, 40° C., gradient: water (+0.1% formic acid): acetonitrile (+0.1% formic acid) at 0 min: 90:10, at 7.5 min 10:90)); MS: (ESI pos.), m/z=no ionization, (ESI neg.), m/z=no ionization.

VI b) 2-Cyano-2-(1,3-dioxo-1,3-dihydro-2H-isoindol-2-yl)ethenyl acetate (E,Z mixture)

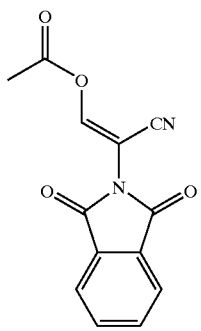

KOtBu (379 mg, 3.55 mmol, 2.2 equivalents) was suspended in THF and, over the course of 10 min, a solution of (1,3dioxo-1,3-dihydro-2H-isoindol-2-yl)acetonitrile (0.30 g, 1.6 mmol) from Example VI a) and ethyl formate (0.29 ml, 0.26 g, 3.6 mmol, 2.2 equivalents) in THF was added. After 2 h at room temperature, the mixture was cooled to 0° C. and a solution of acetic anhydride (0.21 ml, 0.23 g, 2.3 mmol, 1.4 equivalents) and acetic acid (0.18 ml, 0.19 g, 3.2 mmol, 2 equivalents) was added. The mixture was allowed to warm to room temperature and was then stirred for 1 h, and EA and $H_2O$ were added. After phase separation, the organic phases were combined and concentrated in a rotary evaporator.

Yield: 0.36 g (88%).

$R_f$: 0.58 ($CH_2Cl_2$/MeOH 5/1).

MS: (DCI), m/z=274 ($[M+NH_4]^+$).

LCMS: Ret. time: 2.9 min (column: Symmetry, C-18, 3.5 μm, 50×2.1 mm, flow rate 0.5 ml/min, 40° C., gradient: water (+0.1% formic acid): acetonitrile (+0.1% formic acid) at 0 min: 90:10, at 7.5 min 10:90));

MS: (ESI pos.), m/z=256 ($[M+H]^+$).

VIIa. Synthesis of 2-cyano-2-(2-oxo-1,3-oxazolidin-3-yl)ethenyl acetate (E/Z mixture)

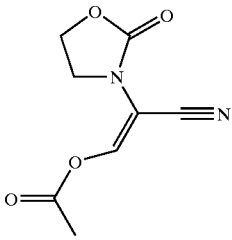

A solution of 4.10 g (32.5 mmol) of (2-oxo-1,3-oxazolidin-3-yl)acetonitrile from Example IV a and 5.30 g (71.5 mmol) of ethyl formate in 20 ml of anhydrous THF was added dropwise to a suspension of 8.03 g (71.5 mmol) of potassium tert-butanolate in 40 ml of anhydrous THF while cooling in ice. The mixture was then stirred at room temperature for 1 h. Then, while cooling in ice, a solution of 4.65 g (4.29 ml=45.5 mmol) of acetic anhydride in 4.30 g (4.09 ml=7.15 mmol) of acetic acid was added dropwise, and the mixture was stirred at room temperature for 40 minutes. The mixture was filtered through a short silica gel frit with dichloromethane/methanol as eluent. The eluent was dried over sodium sulfate and evaporated to dryness in a rotary evaporator at 40° C. The crude product resulted in 57 percent yield and was employed directly in the next reaction.

The following were prepared analogously.

| Ex. | Formula | Yield (%) | Spectroscopic data |
|---|---|---|---|
| VII b (from I i) | | 79 | $R_f$: 0.63 ($CH_2Cl_2$/ MeOH 20:1) |

-continued

| Ex. | Formula | Yield (%) | Spectroscopic data |
|---|---|---|---|
| VII c (from I k) | 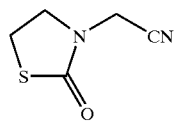 | Reacted as crude product | $R_f$: 0.60 (CH$_2$Cl$_2$/MeOH 20:1) |

VIII. Synthesis of 2-cyano-2-(2-oxo-1,3-thiazolidin-3-yl)ethenyl acetate (E/Z mixture)

VII a) (2-Oxo-1,3-thiazolidin-3-yl)acetonitrile

Preparation took place in analogy to Example IV a from bromoacetonitrile and 2-thiazolidinone. The substance was employed as DMF-containing crude product in the next reaction.

VIII b) 2Cyano-2-(2-oxo-1,3-thiazolidin-3-yl)ethenyl acetate (E/Z mixture)

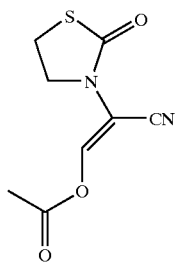

Preparation took place in analogy to Example VII from (2-oxo-1,3-thiazolidin-3-yl)acetonitrile from Example VIIIa, ethyl formate and acetic anhydride. The substance was employed as crude product in the next reaction.

IX. Synthesis of (2E/Z)-3-(dimethylamino)-2-(3,3,4trimethyl-2,5-dioxo-1-pyrrolidinyl)-2propenonitrile

IX a) (3,3,4-Trimethyl-2,5-dioxo-1-pyrrolidinyl)acetonitrile

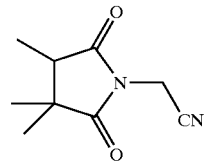

Synthesis took place in analogy to Example VI a from (3,3,4-trimethyl-2,5-dioxo-1-pyrrolidine (obtainable from trimethylsuccinic acid and ammonia as described by Auwers; Oswald; Justus Liebigs Ann. Chem.; 285; 1895; 307; trimethylsuccinic acid can be obtained from 2-bornanone by reaction with nitric acid as described by Bredt; Chem. Ber.; 27; 1894; 2093) and bromoacetonitrile with the exception that acetone was used as solvent in place of DMF. The substance was employed as crude product in the next reaction.

Yield: 99.9%.

GC-MS: $R_t$=8.08 min (method H).

MS (TOF-CI), m/z=181 ([M+H]$^+$).

IX b) (2E/Z)3-(dimethylamino)-2-(3,3,4-trimethyl-2,5-dioxo-1-pyrrolidinyl)-2-propenonitrile

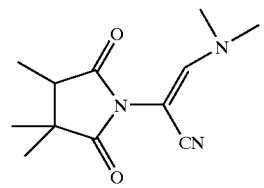

Synthesis took place in analogy to Example II a from (3,3,4trimethyl-2,5dioxo-1-pyrrolidinyl)acetonitrile from Example IX a and tert-butoxybis(dimethylamino)methane.

Yield: 27%.

LC-MS: $R_t$=2.02 min (method E).

MS (ESI pos.), m/z=236 ([M+H]$^+$), 471 ([2M+H]$^+$).

X. Synthesis of 2cyano-2-(1-methyl-2,4-dioxo-3-azabicyclo[3.1.0]hex-3-yl)ethenyl acetate (E/Z mixture)

X a) (1-Methyl-2,4-dioxo-3-azabicyclo[3.1.0]hex-3-yl)acetonitrile

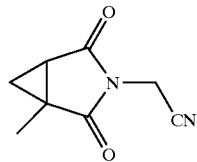

Synthesis took place in analogy to Example VI a from 1-methyl-3-azabicyclo[3.1.0]hexane-2,4-dione (obtainable from 3-methyl-1H-pyrrole-2,5-dione by cyclopropanation by known processes, e.g. as described by Annoura, H.;

Fukunaga, A.; Uesugi, M.; Tasuoka, T.; Horikawa, Y.; Bioorg Med Chem Lett 1996, 6, 763–766) and bromoacetonitrile with the exception that acetone was used as solvent in place of DMF. The substance was employed as crude product in the next reaction.

Yield: 99.8%.

$R_f$: 0.52 (CH$_2$Cl$_2$/MeOH 20:1).

X b) 2-Cyano-2-(1-methyl-2,4 dioxo-3-azabicyclo [3.1.0]hex-3-yl)ethenyl acetate (E/Z mixture)

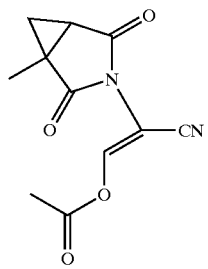

Synthesis took place in analogy to Example VII from (1-methyl-2,4-dioxo-3-azabicyclo[3.1.0]hex-3-yl) acetonitrile from Example X a and ethyl formate, potassium tert-butanolate and acetic anhydride/acetic acid. The substance was employed as crude product in the next reaction.

Yield: 65%.

XI. Synthesis of (E/Z)-2-cyano-2-(3,5-dioxo-10-oxa-4-zatricyclo[5.21.0$^{2,6}$]-dec-4-yl)ethenyl acetate XI a) (3,5-Dioxo-10-oxa-4-azatricyclo[5.2.1.0$^{2,6}$]dec-4-yl)acetonitrile

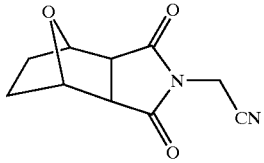

Synthesis took place in analogy to Example VI a from 10-oxa-4-azatricyclo[5.2.1.0$^{2,6}$]decane-3,5-dione (obtainable from maleimide and furan from Diels-Alder reaction for example as described by Padwa, A.; Dimitroff, M.; Waterson, A. G.; Wu, T.; J Org Chem 1997, 62, 4088–4096 and subsequent hydrogenation as described by Ansell, M. F.; Caton, M. P. L.; North, P. C.; Tetrahedron Lett. 1982, 23, 2811) and bromoacetonitrile with the exception that acetone was used as solvent in place of DMF. The substance was employed as crude product in the next reaction.

Yield: 15%.

GC-MS: R$_t$=12.05 min (method H).

MS (TOF-CI), m/z=224 ([M+NH$_4$]$^+$).

XI b) (E/Z)2-Cyano-2-(3,5-dioxo-10-oxa-4-azatzicyclo[5.2.1.0$^{2,6}$]dec-4-yl)ethenyl acetate

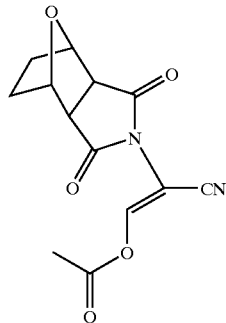

Synthesis took place in analogy to Example VII from (3,5-dioxo-10-oxa-4-azatricyclo[5.2.1.0$^{2,6}$]dec-4-yl) acetonitrile from Example XI a and ethyl formate, potassium tert-butanolate and acetic anhydride/acetic acid. The substance was employed as crude product in the next reaction.

Yield: 61%.

$R_f$: 0.75 (CH$_2$Cl$_2$/MeOH 20:1).

EXAMPLES 1. 4-{4-Amino-2-[1-(2-fluorobenzyl)-1H-pyrazolo [3,4b]pyridin-3-yl]-5-pyrimidinyl}-3-morpholinone

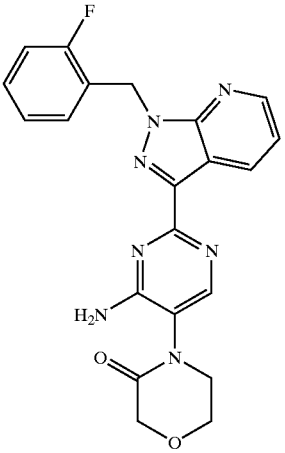

1.50 g (7.68 mmol) of (2)-3-(dimethylamino)-2-(3-oxo-4-morpholinyl)-2-propionitrile (E/Z mixture) from Example II a and 2.48 g (9.22 mmol) of 1-(2-fluorobenzyl)-1H-pyrazolo[3,4-b]pyridine-3carboximidamide from Example V were dissolved in 90 ml of xylene and stirred at 120° C. overnight. The mixture is chromatographed on silica gel with dichloromethane/methanol (gradient 200:1/50:1/20:1).

Yield: 200 mg (5.65%).

Rf: 0.50 (dichloromethane/methanol 10:1).

$^1$H-NMR: (300 MHz, D$_6$-DMSO, δ=3.51–3.60 (br.s, 2H, (CH$_2$N), 3.98–4.06 (br. t, 2H, CH$_2$O), 4.20 (s, 2H, CH$_2$O), 5.83 (s, 2H, CH$_2$), 7.10–7.41 (m, 7H, Ar—H and NH$_2$), 8.24 (s, 1H, pyrimidine H), 8.66 (dd, 1H, pyridine H), 8.96 (dd, 1H, pyridine H).

MS: (ESI pos.), m/z=420 ([M+H]$^+$).

The following were prepared in an analogous way:

| Ex. | Formula | Yield (%) | Spectroscopic data |
|---|---|---|---|
| 2 (from II b) | | 2 | MS-ESI pos. (m/z): 404.2 [M + H]⁺ retention time (min) (Method B): 3.80 Rf CH₂Cl₂/MeOH 10:1:0.49 |
| 3 (from II c) | | 18 | MS-ESI pos. (m/z): 418 [M + H]⁺ retention time (min) (Method A): 2.623 Rf CH₂Cl₂/MeOH 10:1:0.62 |
| 4 (from II d) (racemate) | | 6 (racemate) | MS-ESI pos. (m/z): 418.4 [M + H]⁺ retention time (min) (Method B): 3.86 Rf CH₂Cl₂/MeOH 10:1:0.49 |

| Ex. | Formula | Yield (%) | Spectroscopic data |
| --- | --- | --- | --- |
| 5 (from II e) | | 5 | MS-ESI pos. (m/z): 432 [M + H]+<br>retention time (min) (Method A): 2.699<br>Rf CH$_2$Cl$_2$/MeOH 10:1:0.58 |
| 6 (from II f) | | 2 | MS-ESI pos. (m/z): 432 [M + H]+<br>retention time (min) (Method A): 2.008<br>Rf CH$_2$Cl$_2$/MeOH 20:1:0.25 |
| 7 (from II d) ((+)-enantiomer) | | 2.42 | Retention time (min) (chiral HPLC, Method D): 5.300<br>Rf CH$_2$Cl$_2$/MeOH 10:1:0.49<br>(+)-enantiomer, specific rotation at 20.9° C. and 589 nM: +115.8° |

-continued

| Ex. | Formula | Yield (%) | Spectroscopic data |
| --- | --- | --- | --- |
| 8 (from II d) ((−)-enantiomer) | | 2.55 | Retention time (min) (chiral HPLC, Method D): 6.990<br>Rf CH$_2$Cl$_2$/MeOH 10:1:0.49<br>(−)-enantiomer, specific rotation at 20.8° C. and 589 nM: +113.6° |
| 9 (from II g) | | 3.41 | MS-ESI pos. (m/z): 460 ([M + H]$^+$), 919 ([2M + H]$^+$)<br>retention time (min) (Method E): 2.437<br>Rf (CH$_2$Cl$_2$/MeOH 20:1): 0.49 |
| 10 (from II h) | | 5.62 (a) | MS-ESI pos. (m/z): 418 ([M + H]$^+$), 835 ([2M + H]$^+$)<br>retention time (min) (Method E): 1.999<br>Rf (CH$_2$Cl$_2$/MeOH 20:1): 0.35 |

-continued

| Ex. | Formula | Yield (%) | Spectroscopic data |
| --- | --- | --- | --- |
| 11 (from II k) | | 6 | $R_f$: 0.31 (CH$_2$Cl$_2$/MeOH 20:1) LC-MS: $R_t$ = 2.06 min (Method E). MS (ESI pos.), m/z = 448 ([M + H]$^+$, 895 ([2M + H]$^+$). |
| 12 (from II l) | | 7 | $R_f$: 0.43 (CH$_2$Cl$_2$/MeOH 20:1) $^1$H-NMR: (200 MHz, D$_6$-DMSO), δ = 0.75 – 0.90 (2d, 6H, 2CH$_3$), 1.72 – 1.93 (m, 1H, CH), 4.20 – 4.32 (m, 2H, CH$_2$), 4.50 – 4.63 (m, 1H, CH), 5.91 (s, 2H, CH$_2$), 7.10 – 7.46 (m, 5H, Ar-H and NH$_2$), 7.49 – 7.58 (m, 2H, Ar-H), 8.39 (s, 1H, pyrimidine H), 8.74 (dd, 1H, pyridine H), 8.98 (dd, 1H, pyridine H). LC-MS: $R_t$ = 2.30 min (Method E). MS (ESI pos.), m/z = 448 ([M + H]$^+$), 895 ([2M + H]$^+$). |
| 13 (from IX) | | 6 | $R_f$: 0.24 (CH$_2$Cl$_2$/MeOH 20:1) $^1$H-NMR: (300 MHz, D$_6$-DMSO), δ = 1.13 – 1.25 (d and s, 6H, 2CH$_3$), 1.33 (s, 3H, CH$_3$), 2.98 – 3.16 (m, 1H, CH), 5.91 (s, 2H, CH$_2$), 7.10 – 7.46 (m, 5H, Ar-H), 7.50 – 7.75 (br. s, 2H, NH$_2$), 8.21 (s, 1H, pyrimidine H), 8.64 (dd, 1H, pyridine H), 8.94 (dd, 1H, pyridine H). LC-MS: $R_t$ = 3.73 min (Method G). MS (ESI pos.), m/z = 460 ([M + H]$^+$). |

(a) Racemate

14. 3-{4-Amino-2-[1-(2-fluorobenzyl)-1H-pyrazolo[3,4-b]pyridin-3-yl]-5-pyrimidinyl}-5,5-dimethyl-1,3-oxazolidine-2,4-dione

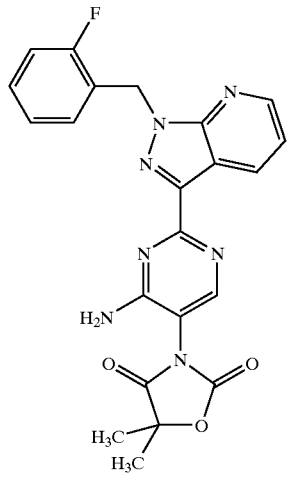

2.30 g (10.3 mmol) of (2)-3-(dimethylamino)2-(5,5-dimethyl-2,4-dioxo-1,3-oxazolidin-3-yl)-2-propionitrile (E/Z mixture) from Example III and 1.39 g (5.15 mmol) of 1-(2-fluorobenzyl)-1H-pyrazolo[3,4-b]pyridine-3-carboximidamide from Examnple V were dissolved in 90 ml of xylene and stirred at 120° C. overnight. The mixture was chromatographed twice on silica gel with dichloromethane/methanol (1st grdient 200:1/50:1/20:1, 2nd gradient 100:1/50:1) and then further purified by preparative HPLC (column: Kromasil 100 C 18 5 μm 250×20 mm No. 101131R, flow rate: 25 ml/min, temp. 50° C., gradient water/acetonitrile at 0 min: 55/45, at 14 min 55/45).

Yield: 33.9 g (1.47%).

$^1$H-NMR: (300 MHz, D$_6$-DMSO), δ=1.69 (s, 6H, CH$_3$), 5.85 (s, 2H, CH$_2$), 7.10–7.26 (m, 3H, Ar—H), 7.30–7.42 (m, 2H, Ar—H), 7.59 (br. s, 2H, NH$_2$), 8.41 (s, 1H, pyrimidine H), 8.66 (dd, 1H, pyridine H), 8.95 (dd, 1H, pyridine H).

MS: (ESI pos.), m/z=448.4 ([M+H]$^+$), 895.6 ([2M+H]$^+$).

15. 3-{4-Amino-2-[1-(2-fluoroenzyl)-1H-pyrazolo[3,4-b]pyridin-3-yl]-5-pyridinyl}-1,3-oazolidin-2-one

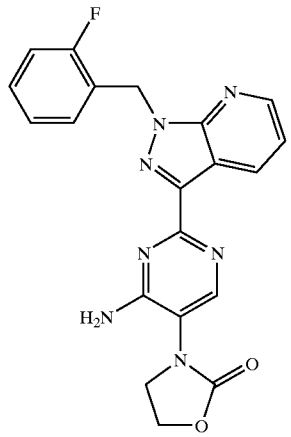

1.14 g (6.29mmol) of (2)-3-(dimethylamino)-2-(2oxo-13-oxazolidin-3-yl)-2-propionitrile (E/Z mixture) from Example IV and 1.69 g (6.29 mmol) of 1-(2-fluorobenzyl)-1H-pyrazolo[3,4-b]pyridine-3carboximidamide from Example V were dissolved in 50ml of xylene and stirred at 120° C. overnight. The mixture was chromatographed on silica gel with dichloromethane/methanol (gradient 100:1/50:1).

Yield: 44.0 g (1.70%).

$^1$H-NMR: (200 MHz, D$_6$-DMSO), δ=3.80 (t, 2H, CH$_2$N), 4.48 (t, 2H, CH$_2$O), 5.82 (s, 2H, CH$_2$), 7.10–7.42 (m, 7H, Ar—H and NH$_2$), 8.40 (s, 1H, pyrimidine H), 8.65 (dd, 1H, pyridine H), 8.95 (dd, 1H, pyridine H).

MS: (ESI pos.), m/z=406 ([M+H]$^+$), 811 ([2M+H]$^+$).

Alternatively were 1.00 g (5.10 mmol) of 2-cyano-2-(2-oxo-1,3-oxazolidin-3-yl)ethenyl acetate (E/Z mixture, containing about 10% DMF) from Example VII a and 1.06 g (3.92 mmol) of 1-(2-fluorobenzyl)-1H-pyrazolo[3,4b]pyridine-3-carboximidamide from Example V were suspended in 5 ml of toluene and stirred at 120° C. overnight. After standing at room temperature for three days, ethyl acetate was added to the mixture which was then concentrated in a rotary evaporator. The residue was filtered with dichloromethane/methanol 10:1 through a short silica gel frit. The filtrate was concentrated in a rotary evaporator and the residue was taken up in CH$_2$Cl$_2$. The solution was filtered through Celite. The product was obtained in the form of a pale beige solid after concentration of the filtrate. The spectroscopic data (1H-NMR, LC-MS-ESI) of the substance obtained in this way are identical with the compound previously prepared from the enamine (Example 4B).

Yield: 629 mg (39.6%).

The reaction can also be carried out with equal success in xylene at 120–140° C. or in acetic acid at 120° C. Addition of Lewis acids is also possible, e.g. zinc(II) acetate, scandium(III) trifluoromethanesulfonate, manganese(II) acetate, cobalt(II) acetate, yttrium(III) trifluoromethanesulfonate, boron trifluoride diethyl ether complex. The purification can also take place by chromatography on silica gel (dichloromethane/methanol (gradient 30:1/20:1)) with, where appropriate, subsequent purification by preparative HPLC (Method G).

The following compounds were prepared in analogy to these alternative preparation processes:

| Ex. | Formula | Yield (%) | Spectroscopic data |
|---|---|---|---|
| 16 (from VIII b) | | 5.81 | $R_f$: 0.34 (CH2Cl$_2$/MeOH 20:1)<br>$^1$H-NMR: (300 MHz, D$_6$-DMSO),<br>δ = 3.57 (t, 2H, (CH$_2$N), 3.88 (t, 2H, CH$_2$S), 5.81 (s, 2H, CH$_2$), 7.10 – 7.42 (m, 7H, Ar-H and NH$_2$), 8.26 (s, 1H, pyrimidine H), 8.65 (dd, 1H, pyridine H), 8.95 (dd, 1H, pyridine H).<br>HPLC:$R_t$ = 3.90 min (Method B).<br>LC-MS: $R_t$ = 3.08 min (Method G).<br>MS (ESI pos.), m/z = 422 ([M + H]$^+$), 843 ([2M + H]$^+$). |
| 17 (from VII b) | | 14 | $R_f$: 0.31 (CH2Cl2/MeOH 20:1)<br>$^1$H-NMR: (300 MHz, D$_6$-DMSO),<br>δ = 1.08 (s, 3H, CH$_3$), 1.39 (s, 3H, CH$_3$), 3.71 (d, AB system, 1H, morpholine 6-H), 3.99 (d, AB system, 1H, morpholinone 6-H), 4.18 (d, AB system, 1H, morpholinone 2-H). 4.29 (d, AB system, 1H, morpholinone 2-H), 5.83 (s, 2H, CH$_2$), 7.10 – 7.45 (m, 7H, Ar-H and NH$_2$), 8.09 (s, 1H, pyrimidine H), 8.66 (dd, 1H, pyridine H), 8.98 (dd, 1H, pyridine H).<br>LC-MS: $R_t$ = 3.07 min (Method G).<br>MS (ESI pos.), m/z = 448 ([M + H]$^+$), 895 ([2M + H]$^+$). |
| 18 (from VII C) | | 2 | $R_f$: 0.32 (CH$_2$Cl$_2$/MeOH 20:1)<br>LC-MS: $R_t$ = 3.00 min (Method G).<br>MS (ESI pos.), m/z = 434 ([M + H]$^+$). |

| Ex. | Formula | Yield (%) | Spectroscopic data |
|---|---|---|---|
| 19 (from X) | | 27 | R$_f$: 0.23 (CH$_2$Cl$_2$/MeOH 20:1) LC-MS: R$_t$ = 2.25 min (Method E). MS (ESI pos.), m/z = 444 ([M + H]$^+$), 887 ([2M + H]$^+$). |
| 20 (from XI) | | 0.5 | R$_f$: 0.42 (CH$_2$Cl$_2$/MeOH 20:1) LC-MS: R$_t$ = 2.33 min (Method E). MS (ESI pos.), m/z = 486 ([M + H]$^+$), 971 ([2M + H]$^+$). |

21. N-[2-[1-(2-Fluorebenzyl)-1H-pyrazolo[34-b]pyridin-3-yl]-5-(2-oxo-1,3-oxazolidin-3-yl)-4-pyrimidinyl]acetamide

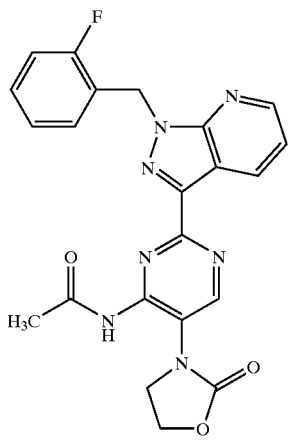

The synthesis took place by the alternative preparation method to Example 15 from 2-cyano-2-(2-oxo-1,3oxazolidin-3-yl)ethenyl acetate (E/Z mixture) from Example VII a and 1-(2-fluorobenzyl)-1H-pyrazolo[3,4-b]pyridine 3-carboximidamide from Example V by stirring in acetic acid at 125° C. for 4 days. Purification took place by preparative HPLC (Method F) The product obtained in this way was suspended in ethyl acetate, filtered off with suction and washed with diethyl ether.

Yield: 4%.

R$_f$: 0.49 (CH$_2$Cl$_2$/MeOH 20:1).

$^1$H-NMR: (300 MHz, D$_6$-DMSO), δ=1.91 (s, 3H, COCH$_3$), 4.13 (t, 2H, CH$_2$N), 4.32 (t, 2H, CH$_2$O), 5.82 (s, 2H, CH$_2$), 7.10–7.44 (m, 5H Ar—H), 8.58 (s, 1H, pyrimidine H), 8.64 (dd, 1H, pyridine H), 8.88 (dd, 1H, pyridine H), 12.18–12.32 (br, s, 1H, NHCO).

LC-MS: R$_t$=3.73 min (Method E).

MS (ESI pos.), m/z=448 ([M+H]$^+$, 895 ([2M+H]$^+$).

22. 2-{4-Amino-2-[1-(2-fluorobenzyl)-1H-pyrazolo[3,4-b]pyridin-3-yl]-5-pyrimidinyl}-1H-isoindole-1,3(2H)-dione

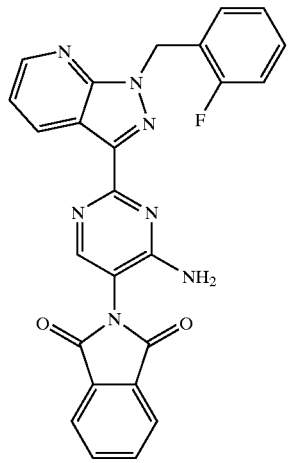

1-(2-Fluorobenzyl)-1H-pyrazolo[3,4-b]pyridine-3-carboximidamide (0.325 g, 1.06 mmol) from Example V, 2-cyano-2-(1,3-dioxo-1,3-dihydro-2H-isoindol-2-yl)ethenyl acetate (E,Z mixture, 0.300 g, 1.17 mmol, 1.1 equivalents) from Example VI and triethylamine (0.30 ml, 0.22 g, 2.1 mmol, 2.0 equiv.) were suspended in toluene and heated under reflux for 9 h. After cooling to room temperature and addition of EA, the precipitate which had separated out was filtered off. The precipitate was purified by preparative HPLC (column: Cromsil 120 ODS, C-18, 10 μm, 250×30 mm, flow rate 50 ml/min, room temperature, gradient: water acetonitrile at 0 min: 90:10, at 28 min 5:95).

Yield: 0.027 g (5%).

$^1$H-NMR: (400 MHz, D$_6$-DMSO), δ=5.86 (s, 2H, OCH$_2$), 7.1–7.3 and 7.32–7.6 (m, 7H, Ar—H, NH$_2$), 7.9–8.0 (m, 4H, Ar—H), 8.32 (s, 1H, Ar—H), 8.65 (d, 1H, Ar—H), 8.98 (d, 1H, Ar—H).

LCMS: Retention time: 3.79 min (column: Symmetry, C-18, 3.5 μm, 50×2.1 mm, flow rate 0.5 ml/min, 40° C., gradient: water (+0.1% formic acid): acetonitrile (+0.1% formic acid) at 0 min: 90:10, at 7.5 min 10:90)); MS: (ESI pos.), m/z=466 ([M+H]$^+$), (ESI neg.), m/z=464 ([M–H]$^+$).

What is claimed is:

1. A compound of the formula (I)

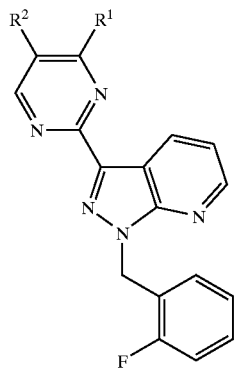

(I)

in which
R$^1$ is NH$_2$ or is NHCO—C$_{1-6}$-alkyl;
R$^2$ is a radical of the formula R$^3$NCOR$^4$ which is bonded via the nitrogen atom to the remainder of the molecule, where
R$^3$ and R$^4$ together with the amide group to which they are bonded form a five- to seven-membered heterocycle which may be saturated or partially unsaturated, may optionally contain a further heteroatom chosen from N, O, and S, and may have 1 to 5 further substituents chosen from oxo, C$_{1-6}$-alkyl, hydroxyl, hydroxy-C$_{1-6}$-alkyl, and halogen, and may be fused to a C$_{6-10}$-aryl ring or to a C$_{3-8}$-cycloalkyl ring in which two carbon atoms are optionally connected together via an oxygen atom;

or a salt, stereoisomer, tautomer, or hydrate thereof.

2. The compound of claim 1,
in which
R$^1$ is NH$_2$ or is NHCO—C$_{1-6}$-alkyl;
R$^2$ is a radical of the formula R$^3$NCOR$^4$ which is bonded via the nitrogen atom to the remainder of the molecule, where
R$^3$ and R$^4$ together with the amide group to which they are bonded form a saturated five- to seven-membered heterocycle which may optionally contain a further heteroatom chosen from N, O, and S, and may have 1 to 5 further substituents chosen from oxo, C$_{1-4}$-alkyl, hydroxyl, hydroxy-C$_{1-4}$-alkyl, and halogen, and may be fused to a C$_{6-10}$-aryl ring or to a C$_{3-8}$-cycloalkyl ring in which two carbon atoms are optionally connected together via an oxygen atom;

or a salt, stereoisomer, tautomer, or hydrate thereof.

3. The compound of claim 1,
in which
R$^1$ is NH$_2$ or is NHCOCH$_3$;
R$^2$ is a radical of the formula R$^3$NCOR$^4$ which is bonded via the nitrogen atom to the remainder of the molecule, where
R$^3$ and R$^4$ together with the amide group to which they are bonded form a saturated five- to seven-membered heterocycle which may optionally contain a further heteroatom chosen from N, O, and S, and may have 1 to 5 further substituents chosen from oxo and C$_{1-4}$-alkyl, and may be fused to a phenyl ring or to a C$_{3-8}$-cycloalkyl ring in which optionally two carbon atoms are connected together via an oxygen atom;

or a salt, stereoisomer, tautomer, or hydrate thereof.

4. The compound of claim 1,
in which
R$^1$ is NH$_2$;
R$^2$ is a radical of the formula R$^3$NCOR$^4$ which is bonded via the nitrogen atom to the remainder of the molecule, where
R$^3$ and R$^4$ together with the amide group to which they are bonded form a five- to seven-membered heterocycle which may be saturated or partially unsaturated, may optionally contain a further heteroatom chosen from N, O, and S, and may have 1 to 5 further substituents chosen from oxo, C$_{1-6}$-alkyl, hydroxyl, hydroxy-C$_{1-6}$-alkyl, and halogen, and may be fused to a C$_{6-10}$-aryl ring;

or a salt, stereoisomer, tautomer, or hydrate thereof.

5. The compound of claim 1,
in which
R$^1$ is NH$_2$;
R$^2$ is a radical of the formula R$^3$NCOR$^4$ which is bonded via the nitrogen atom to the remainder of the molecule, where R³ and R⁴ together with the amide group to which they are bonded form a saturated five- to seven-membered heterocycle, may optionally contain a further oxygen atom and may have 1 to 5 further substituents chosen from oxo, $C_{1-4}$-alkyl, hydroxyl, hydroxy-$C_{1-4}$-alkyl, and F, and may be fused to a $C_{6-10}$-aryl ring;

or a salt, stereoisomer, tautomer, or hydrate thereof.

6. The compound of claim 1, in which

R¹ is $NH_2$;

R² is a radical of the formula R³NCOR⁴ which is bonded via the nitrogen atom to the remainder of the molecule, where R³ and R⁴ together with the amide group to which they are bonded form a five- or six-membered saturated heterocycle which may optionally contain a further oxygen atom and may have 1 to 5 further substituents chosen from oxo and $C_{1-4}$-alkyl, and may be fused to a phenyl ring;

or a salt, stereoisomer, tautomer, or hydrate thereof.

7. A process for preparing compounds of the formula 1 as defined in claim 1, comprising reacting the compound of the formula (II)

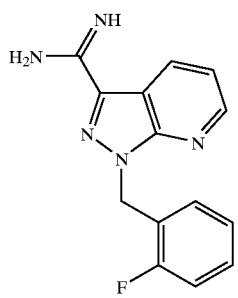

with a compound of the formula (III)

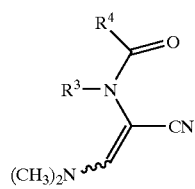

or with a compound of the formula (IV)

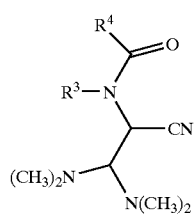

or with a compound of the formula (V)

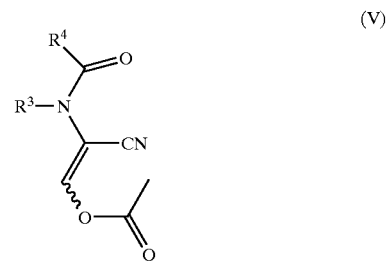

in which R³ and R⁴ have the meaning indicated above in claim 1, in an organic solvent, with heating to give a compound of the formula (I).

8. The process of claim 7 wherein the reaction of a compound of formula (II) with a compound of formula (III), formula (IV), or formula (V) is carried out in the presence of a base.

9. A pharmaceutical composition comprising at least one compound of the formula (I) as defined in claim 1.

10. A pharmaceutical composition comprising at least one compound of the formula (I) as defined in claim 1 in combination with at least one organic nitrate or NO donor.

11. A pharmaceutical composition comprising at least one compound of the formula (I) as defined in claim 1 in combination with at least one compound which inhibits the breakdown of cyclic guanosine monophosphate (cGMP).

12. A method for the treatment of cardiovascular disorders, comprising administering an effective amount of a compound of general formula (I) as defined in claim 1.

13. The method of claim 12, wherein the cardiovascular disorder is hypertension.

14. The method of claim 12, wherein the cardiovascular disorder is chosen from thromboembolic disorders and ischemias.

15. A method for the treatment of sexual dysfunction comprising administering an effective amount of a compound of claim 1.

16. A method for treatment of inflammation comprising administering an effective amount of a compound of general formula (I) as defined in claim 1.

17. A method for treatment of anxiety or depression, comprising administering an effective amount of a compound of general formula (I) as defined in claim 1.

18. The method as claimed in any of claims 12 to 15, where a compound of the geeneral formula (I) as defined in claim 1 is employed in combination with at least one organic nitrate or NO donor or in combination with at least one compound which inhibits the breakdown of cyclic guanosine monophosphate (cGMP).

* * * * *